(12) United States Patent
Janke et al.

(10) Patent No.: US 12,109,389 B2
(45) Date of Patent: Oct. 8, 2024

(54) FLUID PATH ASSEMBLY FOR A DRUG DELIVERY DEVICE

(71) Applicant: AMGEN INC., Thousand Oaks, CA (US)

(72) Inventors: Matthew Wayne Janke, Simi Valley, CA (US); Sudeshna Dutta Ray, Thousand Oaks, CA (US); Scott R. Gibson, Granada Hills, CA (US); Daniel Eduardo Groszmann, Belmont, MA (US); Wael Mismar, Redondo Beach, CA (US); Mehran Mojarrad, Thousand Oaks, CA (US); Robert Allen Dees, San Diego, CA (US); Paul Daniel Faucher, Escondido, CA (US)

(73) Assignee: AMGEN INC., Thousand Oaks, CA (US)

( * ) Notice: Subject to any disclaimer, the term of this patent is extended or adjusted under 35 U.S.C. 154(b) by 922 days.

(21) Appl. No.: 17/256,240

(22) PCT Filed: Jul. 12, 2019

(86) PCT No.: PCT/US2019/041516
§ 371 (c)(1),
(2) Date: Dec. 28, 2020

(87) PCT Pub. No.: WO2020/028009
PCT Pub. Date: Feb. 6, 2020

(65) Prior Publication Data
US 2021/0228797 A1   Jul. 29, 2021

Related U.S. Application Data

(60) Provisional application No. 62/712,638, filed on Jul. 31, 2018.

(51) Int. Cl.
*A61M 5/14* (2006.01)
*A61M 5/145* (2006.01)
(Continued)

(52) U.S. Cl.
CPC ........ *A61M 5/1452* (2013.01); *A61M 5/1626* (2013.01); *A61M 39/221* (2013.01); *A61M 2005/1585* (2013.01); *A61M 2205/52* (2013.01)

(58) Field of Classification Search
CPC .... A61M 5/24; A61M 5/2422; A61M 5/2455; A61M 2005/247; A61M 2005/2474;
(Continued)

(56) References Cited

U.S. PATENT DOCUMENTS 3,636,950 A * 1/1972 Gomez ................ A61M 5/24
604/416
2016/0235959 A1   8/2016 Hu
(Continued)

FOREIGN PATENT DOCUMENTS

WO   WO-9105581 A1   5/1991

OTHER PUBLICATIONS

International Search Report for International Application No. PCT/US2019/041516, dated Oct. 4, 2019.
(Continued)

*Primary Examiner* — Amber R Stiles
(74) *Attorney, Agent, or Firm* — MARSHALL, GERSTEIN & BORUN LLP (57) ABSTRACT

Fluid path assemblies for drug delivery devices and methods of establishing a fluid flow path for drug delivery devices are described that include a needle shield valve member that couples to a reservoir having a needle mounted thereto. The needle shield valve member includes an internal barrier that protects the needle and/or contains a drug within the reser-
(Continued)

voir until activation of the drug delivery device. Upon activation, there is relative movement between the reservoir and needle shield valve member until the needle pierces the barrier to establish a fluid flow path from the reservoir through the needle shield valve member.

20 Claims, 5 Drawing Sheets

(51) Int. Cl.
*A61M 5/162* (2006.01)
*A61M 39/22* (2006.01)
*A61M 5/158* (2006.01)

(58) Field of Classification Search
CPC .............. A61M 5/1626; A61M 39/221; A61M 2005/1585; A61M 2005/3117; A61M 2005/3118; A61M 2005/312; A61M 5/162; A61M 5/28
See application file for complete search history.

(56) References Cited

U.S. PATENT DOCUMENTS

2018/0200147 A1    7/2018 Sanders
2021/0330880 A1* 10/2021 Moberg ................ A61M 39/18

OTHER PUBLICATIONS

Written Opinion for International Application No. PCT/US2019/041516, dated Oct. 4, 2019.

* cited by examiner

FLUID PATH ASSEMBLY FOR A DRUG DELIVERY DEVICE

CROSS-REFERENCE TO RELATED APPLICATION

This is the United States national phase of International Patent Application No. PCT/US19/41516, filed Jul. 12, 2019, which claims priority to U.S. Provisional Patent Application No. 62/712,638, filed Jul. 31, 2018, the entire contents of each of which are hereby incorporated by reference herein.

FIELD OF THE DISCLOSURE

The present disclosure generally relates to drug delivery devices and, more particularly, to fluid path assemblies for drug delivery devices.

BACKGROUND

Some conventional drug delivery devices can utilize a container prefilled with medicament. In such devices, a fill container assembly can be utilized to fluidly couple the container to the rest of a fluid path of the drug delivery device through a crimp interface. This configuration can occupy a relatively large footprint, which decreases available space during sterilization and filling. The drug delivery devices incorporating such configurations may also require larger housings, which raises material, storage, and transportation costs. Further, conventional containers, fill container assemblies, and fluid path assemblies can often include complex components that increase particulate risk and residuals from the sterilization process.

SUMMARY

In accordance with a first aspect, a fluid path assembly for a drug delivery device is described that includes a reservoir having a sidewall that defines an interior for containing a drug and a neck at a first end, a needle that is fixed within the neck of the reservoir with a first end extending forwardly from the reservoir and a second end fluidly connected to the interior of the reservoir, and a needle shield valve member having a body that defines an inlet coupled to the reservoir, an outlet, and a barrier extending between the inlet and the outlet to prevent fluid flow through the body. At least one of the reservoir and the needle shield valve member is movable between a first position where the needle is embedded within or spaced from the barrier and a second position where the needle extends through the barrier to establish a fluid path from the interior of the reservoir to the outlet of the body.

With this configuration, some example fluid path assemblies can include one or more of the following aspects: the reservoir can be movable between the first position and the second position; the needle can be embedded within the barrier in the first position; the reservoir can include a flange that extends outwardly around the first end of the sidewall and the inlet of the needle shield valve member can include a first internal groove to engage the flange in the first position and a second internal groove to engage the flange in the second position; the body of the needle shield valve member can have a compact configuration with an axis of the outlet that is disposed at a ninety degree angle or less with respect to an axis of the inlet; the body of the needle shield valve member can be made of a material permeable by a sterilization gas; or the first end of the sidewall can include an end wall that tapers to the neck and the devices can include a stopper that is disposed within the interior of the reservoir, where the stopper includes a forward surface having a contour complementary to the end wall.

According to some forms, the outlet of the body can include a reduced width needle reception portion, a conduit reception portion, and a shoulder that extends between the conduit reception portion and the needle reception portion. In further forms, the fluid path assemblies can include a conduit that is disposed within the outlet to abut the shoulder.

According to some forms, the fluid path assembly can further include a needle shield cover surrounding at least a portion of the body of the needle shield valve member.

According to some forms, the needle shield cover includes a body having a length greater than that of the needle shield valve member.

According to some forms, the fluid path assemblies can include a drive mechanism that is configured to move at least one of the reservoir and the needle shield valve member from the first position to the second position. In further forms, the fluid path assemblies can be provided in combination with a drug delivery device that includes a housing, a needle insertion mechanism, and a plunger drive mechanism that is configured to selectively drive the stopper through the container to thereby force the medicament from the reservoir with the reservoir in the second position.

In accordance with a second aspect, a method of establishing a fluid flow path in a drug delivery device including a reservoir having a sidewall defining an interior for containing a drug and a first end, a needle fixed within the first end of the reservoir with a first end extending forwardly from the reservoir and a second end fluidly connected to the interior of the reservoir, and a needle shield valve member having a body defining an inlet coupled to the reservoir, an outlet, and a barrier extending between the inlet and the outlet to prevent fluid flow through the body is described. The method includes coupling the reservoir to the inlet of the body in a first position so that a tip of the needle is embedded within or spaced from the barrier, and moving at least one of the reservoir and the needle shield valve member to a second position so that the tip of the needle extends through the barrier to establish a fluid flow path from the interior of the reservoir to the outlet of the body.

According to some forms, example methods can include one or more of the following: coupling the reservoir to the inlet of the body in the first position can include embedding the tip of the needle within the barrier; the reservoir can include a neck at the first end and a flange extending outwardly around the neck and the inlet of the needle shield valve member includes first and second internal grooves, so that coupling the reservoir to the inlet of the body in the first position can include disposing the flange within the first internal groove and moving at least one of the reservoir and the needle shield valve member to the second position can include moving the flange to the second internal groove; the method can include sterilizing the reservoir, needle, and needle shield valve member; the method can include inserting a conduit into the outlet of the needle shield valve member until the conduit abuts a shoulder extending between a conduit reception portion and a needle reception portion of the outlet; or the method can include operating a needle insertion mechanism to insert a cannula into a patient.

According to some forms, the method can include driving a stopper through the reservoir to dispense a drug through the needle and into the outlet of the needle shield valve member. In further forms, driving the stopper through the reservoir can include engaging a tapering end wall of the first end of the reservoir with a forward surface of the stopper having a contour complementary to the end wall such that hold up volume of the drug within the reservoir is limited to drug remaining in the needle.

BRIEF DESCRIPTION OF THE DRAWINGS

The above needs are at least partially met through provision of the embodiments described in the following detailed description, particularly when studied in conjunction with the drawings, wherein.

DETAILED DESCRIPTION

A fluid path assembly for drug delivery devices and methods of establishing a fluid flow path for drug delivery devices are described herein. More specifically, a needle shield valve is provided that couples to a reservoir having a needle mounted thereto. The needle shield valve includes an internal barrier that protects the needle and/or contains a drug within the reservoir until activation of the drug delivery device. Upon activation, the reservoir and needle shield valve move relative to one another until the needle pierces the barrier to establish a fluid flow path from the reservoir through the needle shield valve.

This configuration can provide several advantages over conventional flow paths. In some examples, the material of the primary container can be chosen to minimize sub-visible particle risk and/or the material of the needle shield valve can be a gas permeable elastomer for easy sterilization. In further examples, the fluid path assemblies address challenges associated with the sterilization of conventional crimped glass septum interfaces in cartridge-based primary containers. Further, the fluid path assemblies can significantly reduce a footprint for the drug delivery devices by requiring fewer components to establish the fluid flow path. In some examples, the fluid path assemblies can save up to 7 mm in length as compared to cartridge-based primary containers with a crimped septum, which saves costs throughout the life of the devices, including material, storage, sterilization, and transportation costs.

Figure 1:
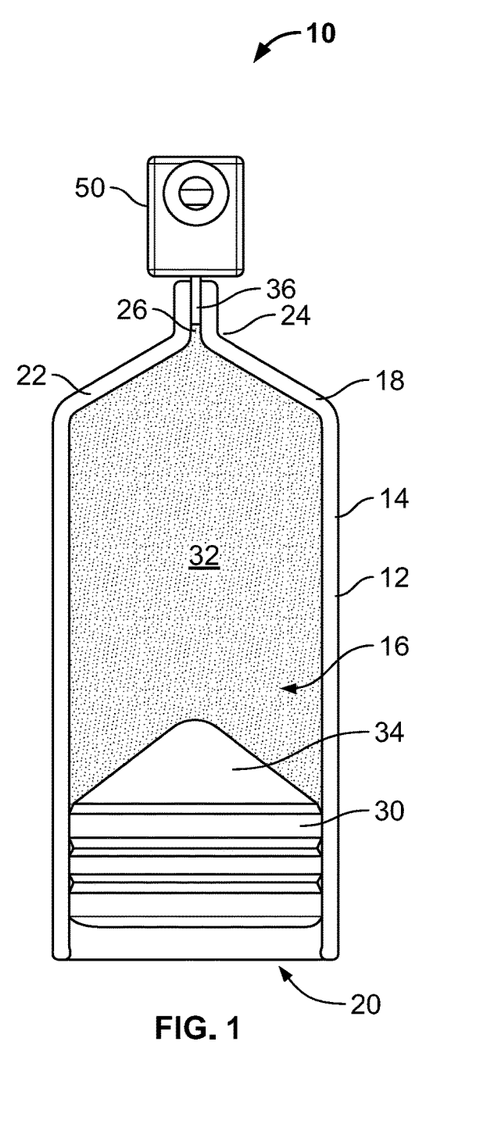
FIG. 1 is a partial cross-sectional side view of an example fluid path assembly including a reservoir and needle shield valve member in accordance with various embodiments.
Figure 2:
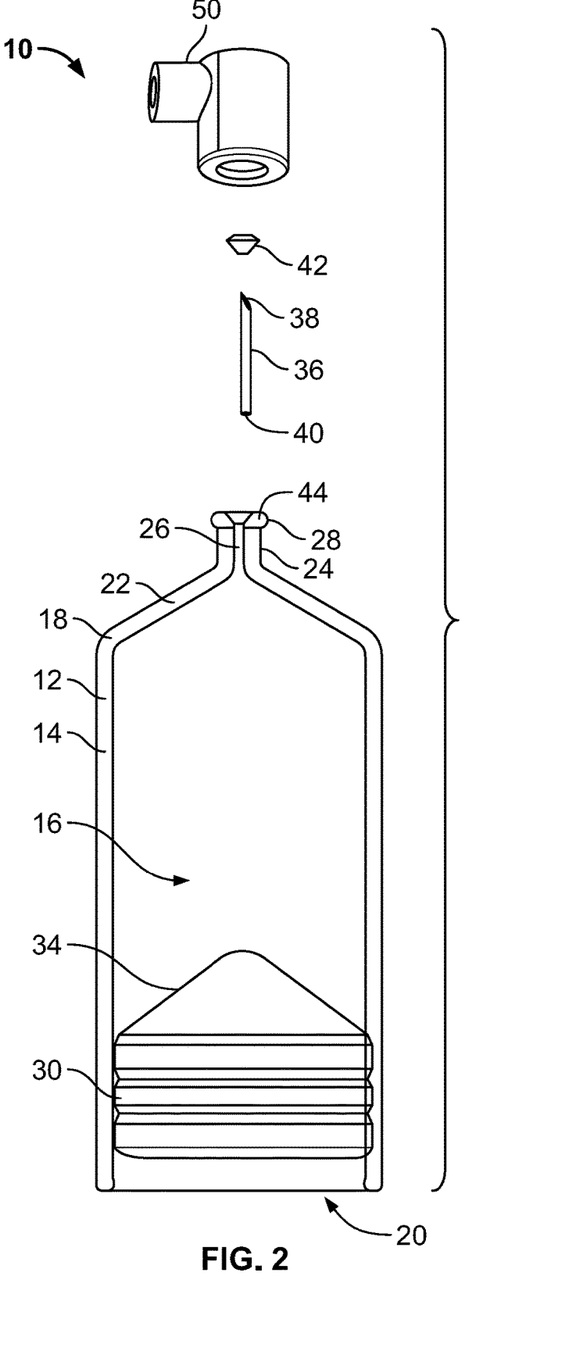
FIG. 2 is an exploded view of the fluid path assembly of FIG. 1.

Details of an example fluid path assembly 10 for a drug delivery device flow path 11 are shown in FIGS. 1 to 6. As shown in FIGS. 1 and 2, the fluid path assembly 10 includes a reservoir 12 having a cylindrical sidewall 14 defining an interior 16 and extending from a first end 18 to an open second end 20. The first end 18 of the reservoir 12 can have an end wall 22 with a tapered configuration, such as conical as shown, that extends to a forwardly extending neck 24 having a passage 26 extending therethrough to the interior 16. An annular flange 28 extends radially around an end of the neck 24. A diameter, width, and/or cross-section of the neck 24 may be smaller than a diameter, width, and/or cross-section of the reservoir 12.

The fluid path assembly 10 further includes a stopper 30 that is disposed within the interior 16 of the reservoir 12 to be moved along a longitudinal axis thereof to expel a drug 32. By one approach, the stopper 30 can include a forward surface 34 that is complementary to the end wall 22 of the reservoir 12 to minimize a hold up volume of the drug 32 within the reservoir 12 after the stopper 30 is driven through the reservoir 12. With such a configuration, the only hold up volume within the reservoir 12 after the stopper 30 is fully driven therethrough would be within the passage 26 of the neck 24 and the needle mounted therein, described below.

A needle 36 is fixed within the passage 26 of the neck 24 such that the needle 36 is prevented from moving relative to the neck 24. The needle 36 includes a first end 38, which may be sharpened, that extends forwardly of the reservoir 12 and a second end 40 that is fluidly coupled to the reservoir interior 16. By one approach, the needle 36 can be secured to the reservoir 12 using a mount 42 disposed within an outwardly opening recess 44 of the neck 24m as can be seen in FIG. 2. The mount 42 can be any suitable material, such as bonding glue and an insert molded member. The needle 24 may also or alternatively be staked or adhered to the neck 24.

The fluid path assembly 10 further includes a needle shield valve member 50 that couples to the neck 24 of the reservoir 12 to act as a valve and needle shield. Details of the needle shield valve member 50 are shown in FIGS. 3-6. The needle shield valve member 50 includes a body 52 having an inlet recess 54, an outlet recess 56, and a barrier 58 separating the inlet 54 and outlet 56 and preventing fluid flow through the body 52. The needle shield valve member 50, or the barrier 58 thereof, may be made, partially or entirely, of a flexible or elastically deformable material such as an elastomer or rubber, for example, which is capable of being penetrated or pierced by the sharpened first end 38 of the needle 36. In some versions, the needle shield valve member 50 can have a single piece construction with the inlet 54 engaging the reservoir 12 and the outlet 56 directing fluid flow being portions of the same body. The needle shield valve member 50 can be constructed by any suitable method, such as 3D printing, injection molding, etc. In other versions described further below in reference to FIGS. 7, 8A, and 8B, the needle shield valve member 50 can be constructed of an elastomeric or rubber body surrounded by a rigid plastic needle shield cover or casing, which provides stability to the elastomeric needle shield and secures it in place. This could be designed with an ethylene oxide (ETO) permeable plastic or with spaces which allow ETO to reach the needle shield.

Figure 3:
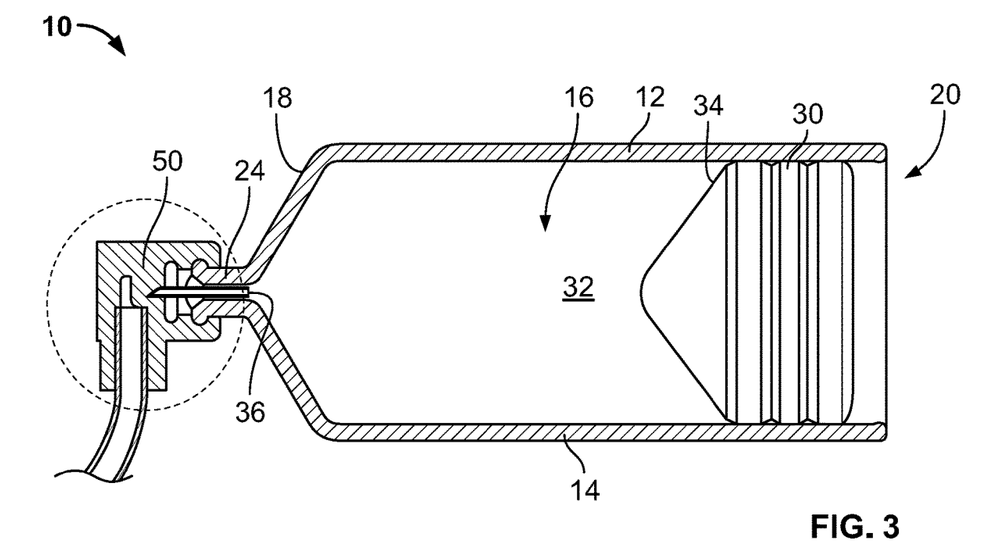
FIG. 3 is a cross-sectional view of the fluid path assembly of FIG. 1 showing the assembly in a storage position.

As shown in FIG. 3, the reservoir 12 couples to the inlet 54 of the needle shield valve member 50 with the neck 24 inserted into the body 52. In some versions, the inlet 54 has a cylindrical interior 60 with first and second annular grooves 62, 64 that are axially spaced from one another with the first groove 62 disposed in closer proximity to an entrance 66 of the inlet 54 and the second groove 64 disposed adjacent to the barrier 58. The first and second grooves 62, 64 are sized to sealingly receive the annular flange 28 of the neck 24 while a diameter of the inlet 54 adjacent to the grooves 62, 64 may be sized to sealingly engage an exterior surface of the neck 24. So configured, the engagement between the body 52 and neck 24 maintains sterility of the fluid flow path 11. If desired, the second groove 64 can include a surface of the barrier 58 such that with the flange 28 received therein, the neck 24 rests against the barrier 58. In other versions, the inlet 54 can be provided without the grooves 62, 64 and the interior 60 of the inlet 54 can have a cylindrical configuration with the neck 24 of the reservoir 12 sized to sealingly slide along the interior surface to maintain sterility.

The outlet 56 includes a proximal portion 68 aligned axially with the inlet 54 on an opposite side of the barrier 58 and a distal portion 70 that extends to an exit 72 from the body 52. The proximal portion 68 has a reduced cross-section with respect to the distal portion 70, such that a shoulder 74 extends within the outlet 56 between the proximal and distal portions 68, 70. In the illustrated form, the distal portion 70 has a cylindrical configuration and the proximal portion 68 has a portion of a cylindrical configuration with a dome-shaped, semi-circular-shaped, or crescent shaped cross-section. So configured, a conduit 76 of the flow path 11 can be inserted into the outlet 56 until an end of the conduit 76 abuts the shoulder 74. In the illustrated form, the body 52 has a compact, bent configuration with an axis of the inlet 54 and an axis of the outlet 56 extending in directions at an angle with respect to one another. For example, the axis of the inlet 54 can be disposed at an approximately 90 degree angle, less than a 90 degree angle, or greater than a 90 degree angle with respect to an axis of the outlet 56. In other approaches, such as for autoinjector drug delivery devices discussed in more detail below, the needle shield valve member 50 can have a generally linear configuration with the inlet 54 and outlet 56 generally aligned along an axis of the body 52.

As shown in FIGS. 3 to 6, the fluid path assembly 10 is configured to be moved from a storage state (FIGS. 3 and 4), in which the flow path 11 is closed, and a use state (FIGS. 5 and 6), in which the flow path 11 is open. As previously discussed, to put the assembly 10 together, the neck 24 of the reservoir 12 is inserted into the inlet 54 until the flange 28 is seated within the first groove 62 so that the reservoir 12 is in a first position. This configuration corresponds to the assembly 10 being in the storage state because the needle 36 has not pierced or has not fully penetrated the barrier 58, preventing fluid flow through the body 52 with the outlet 56 being a plenum. If desired, the body 52, and specifically, the inlet 54 and barrier 58 can be sized so that the first end 38 of the needle 36 is embedded within the barrier 58 in the storage state, as depicted. With this configuration, the needle shield valve member 50 can act as a needle shield to maintain sterility and closed container integrity (CCI) of the needle 36 and reservoir 12. Of course, in other approaches, the first end 38 of the needle 36 can be spaced away from the barrier 58 in the storage state.

Figure 5:
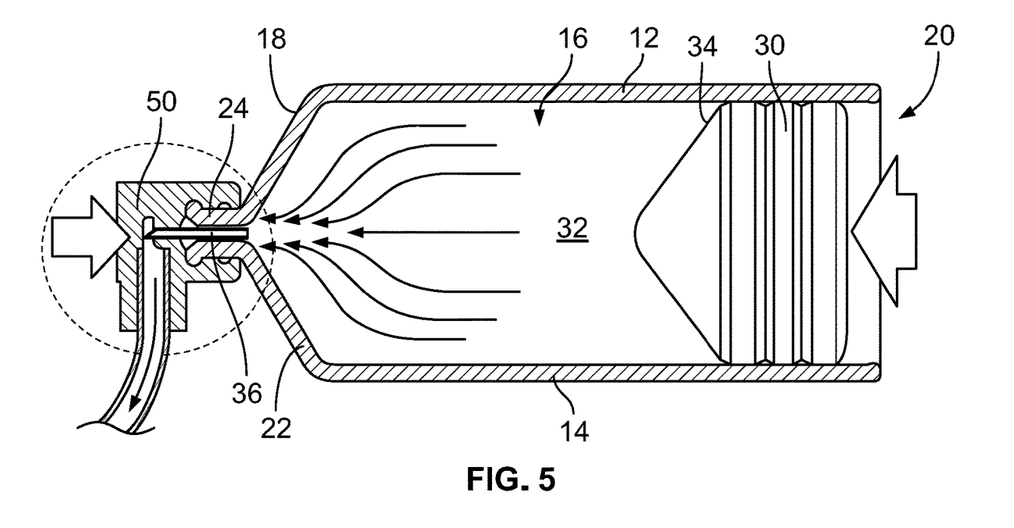
FIG. 5 is a cross-sectional view of the fluid path assembly of FIG. 1 showing the assembly in a use position.
Figure 6:
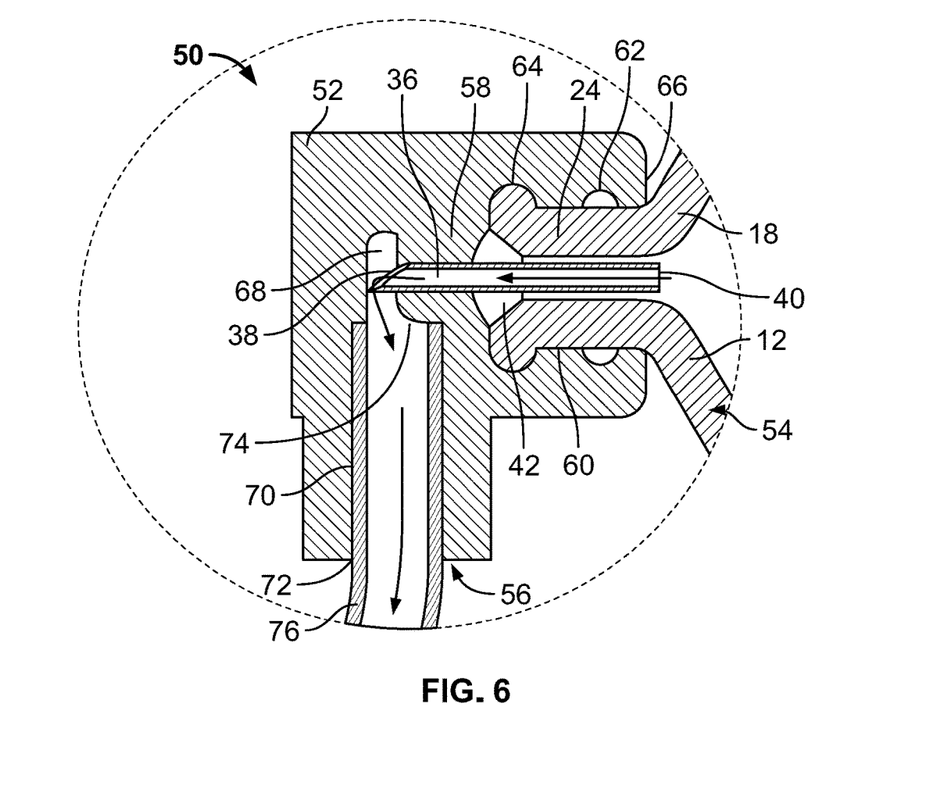
FIG. 6 is a partial view of FIG. 5.

Upon activation, there is relative movement between the reservoir 12 and needle shield valve member 50 so that the flange 28 is dislodged from the first groove 62 and relocated to the second groove 64, thereby placing the reservoir 12 in a second position. In some versions, upon activation, the reservoir 12 is moved towards the needle shield valve member 50 via a drive mechanism applying a motive force to the reservoir. In other versions, the needle shield valve member 50 is moved towards the reservoir 12 via a drive mechanism applying a motive force to the needle shield valve member 50. In yet further versions, both the reservoir 12 and needle shield valve member 50 are moved toward one another, for example, via one or more drive mechanisms applying motive forces to the both the reservoir 12 and the needle shield valve member 50. Moving the reservoir 12 and/or needle shield valve member 50 can be performed by any one or more suitable drive mechanisms, including, for example, a spring, a plunger rod, pressurized gas, motor, and/or a phase changing material. Further, whether held stationary or moved, the reservoir 12 and/or needle shield valve member 50 may be inserted into recesses or engaged by walls of a drug delivery device to hold and orient the reservoir 12 and/or needle shield valve member 50 during storage and operation. The reservoir 12 and/or needle shield valve member 50 can be secured in place by adhesive, friction fit, press fit, retaining walls, and so forth. As shown in FIGS. 5 and 6, as the reservoir 12 is moved so that the flange 28 is shifted from the first groove 62 to the second groove 64, the first end 38 of the needle 36 is driven through the barrier 58 into the proximal portion 68 of the outlet 56. With the assembly 10 in the use state, the fluid path 11 extends from the reservoir interior 16, through the needle 36, through the outlet 56 of the needle shield valve member 50, and into the conduit 76.

The fluid path assembly described herein provides a simple piercing interconnection enabled by the needle shield valve member 50. The needle shield valve member 50 can be made of an elastomer suitable for sealingly engaging the reservoir flange 28, as well as for having the end 38 of the needle 36 embedded therein and being pierced by the needle 36. Further, the elastomer of the needle shield valve member 50 can be ethylene oxide (ETO) permeable for convenient sterilization. Additionally, in some embodiments, the material used to construct the needle shield valve member 50 may be permeable to any one of or any combination of the gaseous sterilizing agents chosen from the following non-exclusive list of gaseous sterilizing agents: ethylene oxide (EtO), ozone, chlorine dioxide, nitrogen dioxide, and steam (e.g., pressurized water vapor). In some embodiments, the material used to construct the needle shield valve member 50 may be an elastomer material that is permeable to EtO. The needle shield valve member 50 may be subjected to a gaseous sterilization treatment after the neck 24 of the reservoir 12 has been tightly inserted into the inlet 54. By constructing the needle shield valve member 50 of a material that is permeable to a gaseous sterilizing agent, less exposure time may be needed for sterilizing the interior surfaces of the inlet 54, outlet 56, and barrier 58 of the fluid path member 58, the needle 36 projecting forwardly of the neck 24, and/or the space or gap between the neck 24 of the reservoir 12 and the barrier 58 with the gaseous sterilization agent. This is because the gaseous sterilizing agent may be able to diffuse through the fluid path member 58 to reach the interior surfaces thereof.

In some examples, the reservoir 12 can be sized to contain any desired amount of drug, such as between 1 mL to 20 mL, with an example 3 mL example shown in the figures. The volume of the drug 32 contained in the reservoir 12 prior to delivery may be: any volume in a range between approximately (e.g., ±10%) 0.5-20 mL, or any volume in a range between approximately (e.g., ±10%) 0.5-10 mL, or any volume in a range between approximately (e.g., ±10%) 1-10 mL, or any volume in a range between approximately (e.g., ±10%) 1-8 mL, or any volume in a range between approximately (e.g., ±10%) 1-5 mL, or any volume in a range between approximately (e.g., ±10%) 1-3.5 mL, or any volume in a range between approximately (e.g., ±10%) 1-3 mL, or any volume in a range between approximately (e.g., ±10%) 1-2.5 mL, or any volume in a range between approximately (e.g., ±10%) 1-2 mL, or any volume equal to or less than approximately (e.g., ±10%) 4 mL, or any volume equal to or less than approximately (e.g., ±10%) 3.5 mL, or any volume equal to or less than approximately (e.g., ±10%) 3 mL, or any volume equal to or less than approximately (e.g., ±10%) 2.5 mL, or any volume equal to or less than approximately (e.g., ±10%) 2 mL, or any volume equal to or less than approximately (e.g., ±10%) 1.5 mL, or any volume equal to or less than approximately (e.g., ±10%) 1 mL, or any volume equal to or greater than approximately (e.g., ±10%) 2 mL, or any volume equal to or greater than approximately (e.g., ±10%) 2.5 mL, or any volume equal to or greater than approximately (e.g., ±10%) 3 mL. The reservoir 12 may be completely or partially filled with the drug 32. The drug 32 may be one or more of the drugs listed below under the heading "Drug Information."

The material of the reservoir 12 can be a cyclo olefin polymer (COP) or Cyclic Olefin Co-polymer (COC), particularly suitable for reservoirs of 2 mL or more, or glass, particularly suitable for reservoirs of 3 mL to 1 mL or less, but suitable also for up to 20 mL or more. The material can advantageously be selected based on the target volume of the drug 32 to be dispensed to minimize the risk around sub-visible particles. In some examples, the needle 36 can be a non-coring 25G hypo tube needle. In further examples, the needle can be a Tuohy needle design.

Figure 7:
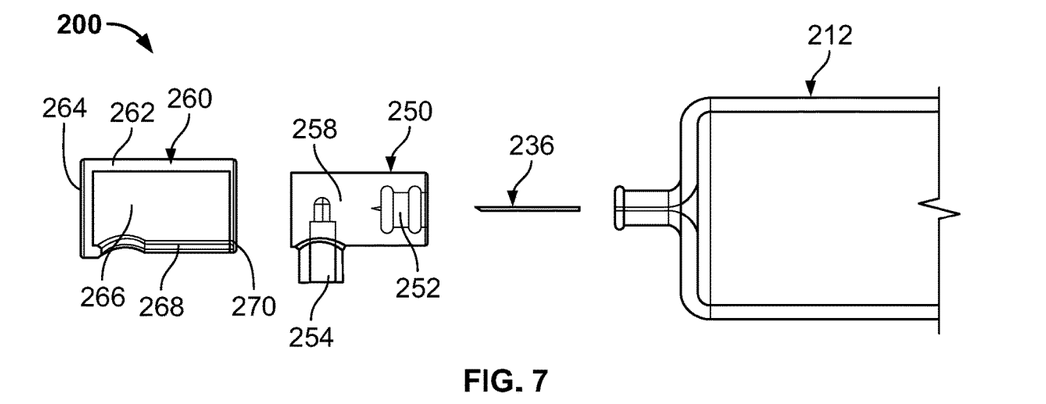
FIG. 7 is an exploded side view of an alternative example of a fluid path assembly including a reservoir, needle shield valve member, and needle shield cover in accordance with various embodiments.
Figure 8A:
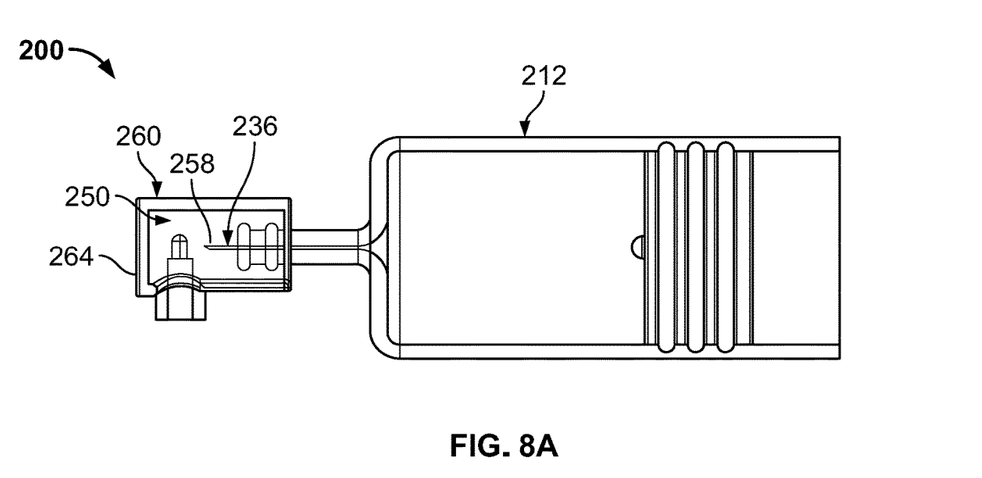
FIG. 8A is a side view of the fluid path assembly of FIG. 7 in an assembled configuration and occupying a storage state.
Figure 8B:
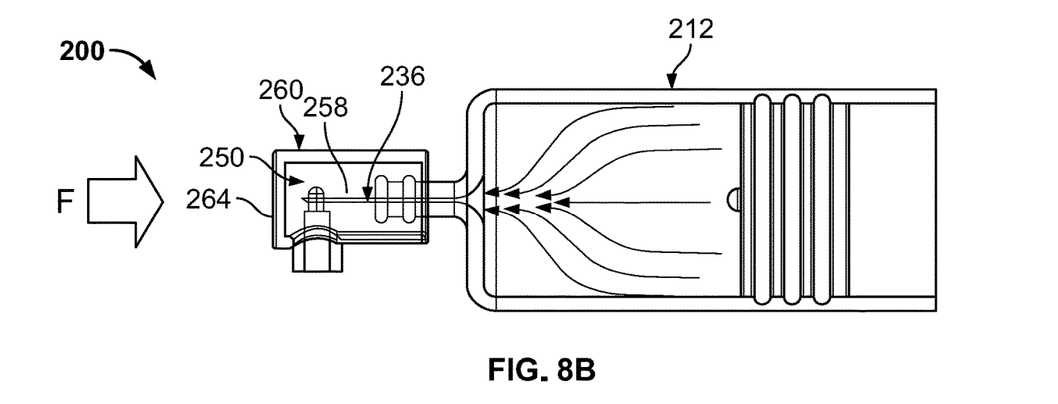
FIG. 8B is a side view of the fluid path assembly of FIGS. 7 and 8A in an assembled configuration and occupying a use state.

As briefly mentioned above, some alternative examples of the fluid path assembly 10 of the present disclosure can also include a rigid plastic needle shield cover, which can also be referred to as a casing, arranged over the body 52 of the needle shield valve member 50. FIGS. 7, 8A and 8B illustrate one such example of a fluid path assembly 200 including a reservoir 212, a needle 236, a needle shield valve member 250, and a needle shield cover 260. The needle shield valve member 250 includes a body 252 defining an inlet recess 252 and an outlet recess 254, and a barrier 258 disposed between the inlet and outlet recesses 252, 254. The reservoir 212, needle 236, and needle shield valve member 250 in FIGS. 7, 8A, and 8B can be similar or identical to any of the corresponding components described above in reference to FIGS. 1-6 and, as such, all the specific details will not be repeated. The needle shield cover 260, as suggested, may include a rigid plastic structure adapted to surround, protect, and provide added structural integrity to the needle shield valve member 250 and therefore the assembly 200 as a whole. In some versions, the shield cover 260 could be constructed of an ethylene oxide (ETO) permeable plastic or with openings or spaces that allow ETO to reach the needle shield valve member 250 during a sterilization process.

Referring to FIG. 7, the needle shield cover 260 includes a generally hollow cylindrical body including a sidewall 262, an end wall 264, an internal cavity 266, a slotted opening 268, and an open end 270. As depicted in FIGS. 8A and 8B, the internal cavity 266 is sized and configured to receive portions of the needle shield valve member 250 including the inlet recess 252 and the barrier 258. In the depicted version, the body of the needle shield cover 260 is sufficiently sized to provide a rigid body extending all or substantially all along the length of the needle shield valve member 250. In some versions, the body of the needle shield cover 260 has a length greater than a corresponding length of the needle shield valve member 250. Additionally, in the depicted version, the portion of the needle shield valve member 250 defining the outlet recess 254 extends out of the slotted opening 268 the needle shield cover 260 and is therefore not covered. In fact, the slotted opening 268 in this version extends from a location proximate to the end wall 264 entirely to the open end 270 such that the needle shield cover 260 can be slid onto the needle shield valve member 250 during assembly. In some forms, the needle shield cover 260 is fixed to the needle shield valve member 250 with friction fit, adhesive, sonic welding, or some other mechanism. In other forms, the needle shield cover 260 could be designed to also receive the portion of the needle shield valve member 250 defining the outlet recess 254 extends out of the needle shield cover 260.

Referring to FIGS. 8A and 8B, once the needle shield cover 260 is assembled onto the needle shield valve member 250 and the assembly 200 is assembled with the needle 238 and reservoir 212, the system functions in a manner essential identical that described above with reference to FIGS. 1-6. FIG. 8A depicts the assembly 200 in a storage state where the needle 236 does not penetrate the barrier 258 of the needle shield valve member 250. FIG. 8B depicts the assembly 200 in a use state where the needle in fact penetrates the barrier 258 to establish an open fluid path. To move from the storage state (FIG. 8A) to the use state (FIG. 8B), there is relative movement between the reservoir 212 and needle shield valve member 250 in a manner same as that described above. For example, in some versions, the reservoir 212 is moved towards the needle shield valve member 250 via a drive mechanism applying a motive force to the reservoir. In other versions, the needle shield valve member 250 is moved towards the reservoir 212 via a drive mechanism applying a motive force to the needle shield valve member 250. In yet further versions, both the reservoir 212 and needle shield valve member 250 are moved toward one another, for example, via one or more drive mechanisms applying motive forces to the both the reservoir 212 and the needle shield valve member 250. Moving the reservoir 212 and/or needle shield valve member 250 can be performed by any one or more suitable drive mechanisms, including, for example, a spring, a plunger rod, pressurized gas, motor, and/or a phase changing material. In those versions where the needle shield valve member 250 receives a motive force F (as shown in FIG. 8B) from a drive mechanism, the end wall 264 of the rigid needle shield cover 260 can serve as a solid foundation for receiving the transfer of force from a plunger, a spring, a gas drive mechanism or otherwise. In this manner, the end wall 264 can be referred to as a hard stop and/or a spring seat for effecting relative movement of the fluid path assembly 200 relative to the needle 236 and/or reservoir 212. Thus, the version of the assembly 200 described in FIGS. 7, 8A, and 8B can have the added benefit of more efficient force transfer in these scenarios, and the needle shield cover 260 can also serve to protect the more deformable material of the needle shield valve member 250 from mechanical degradation.

Figure 9:
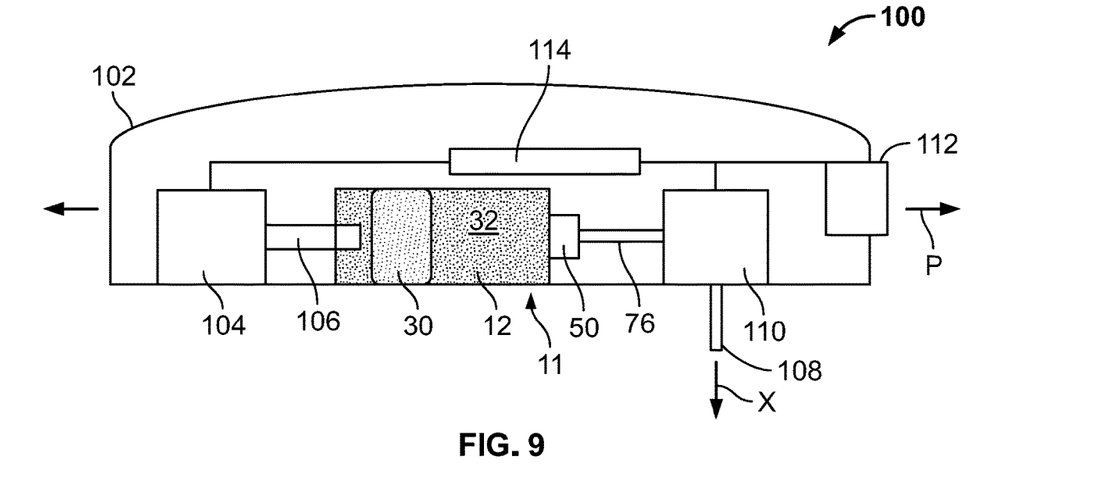
FIG. 9 is a diagrammatic view of an example on-body injector drug delivery device in accordance with various embodiments.

The fluid path assembly 10 can provide a prefilled syringe (PFS)-based primary container and fluid path for a drug delivery device. In a first form, as illustrated in FIG. 9, the drug delivery device can be an on-body injector 100, which has a horizontally oriented configuration with drug delivery components disposed generally along a horizontal plane P within a housing 102 thereof. The drug delivery components of the injector 100 can include the reservoir 12 having the drug 32 contained therein, the stopper 30 disposed within the reservoir 12 and sildably movable therein along the horizontal plane P, a drive mechanism 104 coupled to a plunger 106 to drive the stopper 30 through the reservoir 12, an injection needle or trocar and cannula 108 oriented along an axis X that extends generally perpendicular to the horizontal plane P, the needle shield valve member 50, the flow path 11 fluidly coupling the reservoir 12 to the needle 108, and a needle insertion mechanism 110, such as a scotch yoke mechanism, configured to insert the needle 108 to a desired subcutaneous depth within the user. As commonly configured, one or more of the components of the injector 100, such as the drive mechanism 104 and needle insertion mechanism 110, can be operable in response to actuation of a user input device 112, such as a switch, touch screen, sensor, etc., accessible on an exterior of the housing 102. Pursuant to this, the injector 100 can include electronic components, such as a controller 114, to control operation of one or more of the drug delivery components. The controller 114 can include a processor and a memory storing logic that is executable by the processor. More specifically, the memory may include one or more tangible non-transitory readable memories having logic (e.g., executable instructions) stored thereon, which instructions when executed by the processor may cause the at least one processor to carry out the actions that the controller is adapted to perform. Additionally, the controller 114 may include other circuitry for carrying out certain actions in accordance with the principles of the present disclosure. Suitable drive mechanisms include, but are not limited to, springs, gas sources, phase changing materials, motors, or other electromechanical systems.

Figure 10:
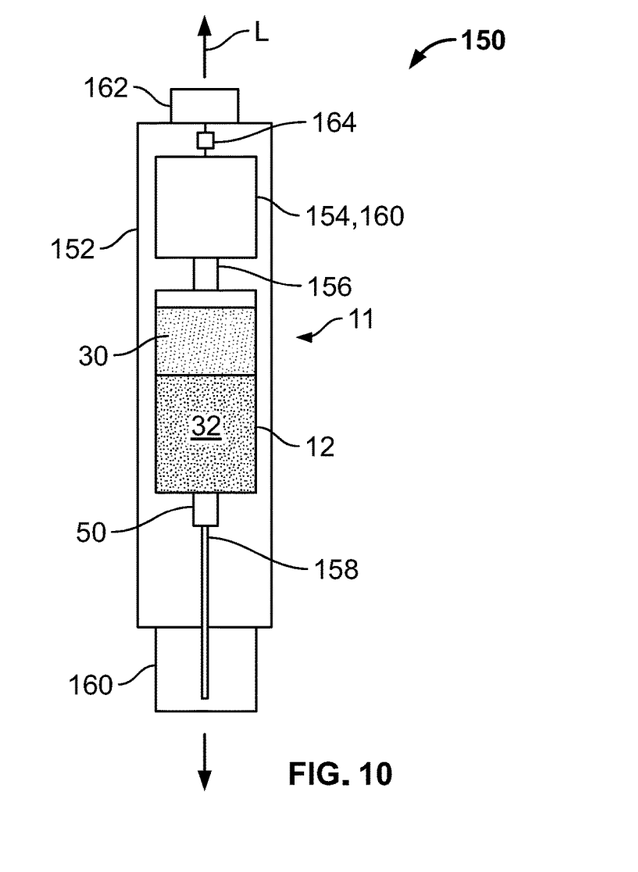
FIG. 10 is a diagrammatic view of an example autoinjector drug delivery device in accordance with various embodiments.

In a second form, as illustrated in FIG. 10, the drug delivery device can be an autoinjector 150 having a vertically oriented configuration with some or all drug delivery components disposed in stacked relation along a longitudinal axis L within a housing 152 of the autoinjector 150. More specifically, the autoinjector 150 can be configured to operate and inject a user with the housing 152 oriented generally perpendicular to a skin surface of the user. The drug delivery components can include the reservoir 12 having the drug 32 contained therein, the stopper 30 disposed within the reservoir 12 and sildably movable therein along the longitudinal axis L, a drive mechanism 154 coupled to a plunger 156 to drive the stopper 30 through the reservoir 12, the needle shield valve member 50, an injection needle or trocar and cannula 158 oriented along the longitudinal axis L, the flow path 11 fluidly coupling the reservoir 12 to the needle 158, and a needle insertion mechanism 160 configured to insert the needle 158 to a desired subcutaneous depth within the user. By some approaches, the needle insertion mechanism 160 can be a retractable needle guard to expose the needle 158 or a drive mechanism to longitudinally move the needle a desired distance. For example, the drive mechanism 154 can be configured to drive both movement of the stopper 30 and the needle 158 by moving some or all of the reservoir 12, flow path 11, and needle 158. As commonly configured, one or more of the components of the autoinjector 150, such as the drive mechanism 154 and needle insertion mechanism 160, can be operable in response to actuation of a user input device 162, such as a switch, touch screen, sensor, etc., accessible on an exterior of the housing 152. Suitable drive mechanisms include, but are not limited to, springs, gas sources, phase changing materials, motors, or other electromechanical systems. Pursuant to this, the autoinjector 150 can include electronic components, such as a controller 164, to control operation of one or more of the drug delivery components. The controller 164 can include a processor and a memory storing logic that is executable by the processor. More specifically, the memory may include one or more tangible non-transitory readable memories having logic (e.g., executable instructions) stored thereon, which instructions when executed by the processor may cause the at least one processor to carry out the actions that the controller is adapted to perform. Additionally, the controller 164 may include other circuitry for carrying out certain actions in accordance with the principles of the present disclosure. Suitable drive mechanisms include, but are not limited to, springs, gas sources, phase changing materials, motors, or other electromechanical systems.

While the injectors of FIGS. 9 and 10 have been described as including the fluid path assembly 10, as referenced in FIGS. 1-6, the injectors of FIGS. 9 and 10 could also include the fluid path assembly 200 in FIGS. 7, 8A, and 8B.

It will be appreciated that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments. The same reference numbers may be used to describe like or similar parts. Further, while several examples have been disclosed herein, any features from any examples may be combined with or replaced by other features from other examples. Moreover, while several examples have been disclosed herein, changes may be made to the disclosed examples within departing from the scope of the claims.

Drug Information

The above description describes various components, assemblies, drug delivery devices, and methods for use with a drug delivery device. It should be clear that the components, assemblies, drug delivery devices, or methods can further comprise use of a medicament listed below with the caveat that the following list should neither be considered to be all inclusive nor limiting. The medicament will be contained in a reservoir. In some instances, the reservoir is a primary container that is either filled or pre-filled for treatment with the medicament. The primary container can be a cartridge or a pre-filled syringe.

For example, the drug delivery device or more specifically the reservoir of the device may be filled with colony stimulating factors, such as granulocyte colony-stimulating factor (G-CSF). Such G-CSF agents include, but are not limited to, Neupogen® (filgrastim) and Neulasta® (pegfilgrastim). In various other embodiments, the drug delivery device may be used with various pharmaceutical products, such as an erythropoiesis stimulating agent (ESA), which may be in a liquid or a lyophilized form. An ESA is any molecule that stimulates erythropoiesis, such as Epogen® (epoetin alfa), Aranesp® (darbepoetin alfa), Dynepo® (epoetin delta), Mircera® (methyoxy polyethylene glycol-epoetin beta), Hematide®, MRK-2578, INS-22, Retacrit®) (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin zeta, epoetin theta, and epoetin delta, as well as the molecules or variants or analogs thereof as disclosed in the following patents or patent applications, each of which is herein incorporated by reference in its entirety: U.S. Pat. Nos. 4,703,008; 5,441,868; 5,547,933;

5,618,698; 5,621,080; 5,756,349; 5,767,078; 5,773,569; 5,955,422; 5,986,047; 6,583,272; 7,084,245; and 7,271,689; and PCT Publication Nos. WO 91/05867; WO 95/05465; WO 96/40772; WO 00/24893; WO 01/81405; and WO 2007/136752.

An ESA can be an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (including EMP1/hematide), and mimetic antibodies. Exemplary erythropoiesis stimulating proteins include erythropoietin, darbepoetin, erythropoietin agonist variants, and peptides or antibodies that bind and activate erythropoietin receptor (and include compounds reported in U.S. Publication Nos. 2003/0215444 and 2006/0040858, the disclosures of each of which is incorporated herein by reference in its entirety) as well as erythropoietin molecules or variants or analogs thereof as disclosed in the following patents or patent applications, which are each herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,830,851; 5,856,298; 5,986,047; 6,030,086; 6,310,078; 6,391,633; 6,583,272; 6,586,398; 6,900,292; 6,750,369; 7,030,226; 7,084,245; and 7,217,689; U.S. Publication Nos. 2002/0155998; 2003/0077753; 2003/0082749; 2003/0143202; 2004/0009902; 2004/0071694; 2004/0091961; 2004/0143857; 2004/0157293; 2004/0175379; 2004/0175824; 2004/0229318; 2004/0248815; 2004/0266690; 2005/0019914; 2005/0026834; 2005/0096461; 2005/0107297; 2005/0107591; 2005/0124045; 2005/0124564; 2005/0137329; 2005/0142642; 2005/0143292; 2005/0153879; 2005/0158822; 2005/0158832; 2005/0170457; 2005/0181359; 2005/0181482; 2005/0192211; 2005/0202538; 2005/0227289; 2005/0244409; 2006/0088906; and 2006/0111279; and PCT Publication Nos. WO 91/05867; WO 95/05465; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; and WO 2006/29094.

Examples of other pharmaceutical products for use with the device may include, but are not limited to, antibodies such as Vectibix® (panitumumab), Xgeva™ (denosumab) and Prolia™ (denosamab); other biological agents such as Enbrel® (etanercept, TNF-receptor/Fc fusion protein, TNF blocker), Neulasta® (pegfilgrastim, pegylated filgrastim, pegylated G-CSF, pegylated hu-Met-G-CSF), Neupogen® (filgrastim, G-CSF, hu-MetG-CSF), and Nplate® (romiplostim); small molecule drugs such as Sensipar® (cinacalcet). The device may also be used with a therapeutic antibody, a polypeptide, a protein or other chemical, such as an iron, for example, ferumoxytol, iron dextrans, ferric glyconate, and iron sucrose. The pharmaceutical product may be in liquid form, or reconstituted from lyophilized form.

Figure 4:
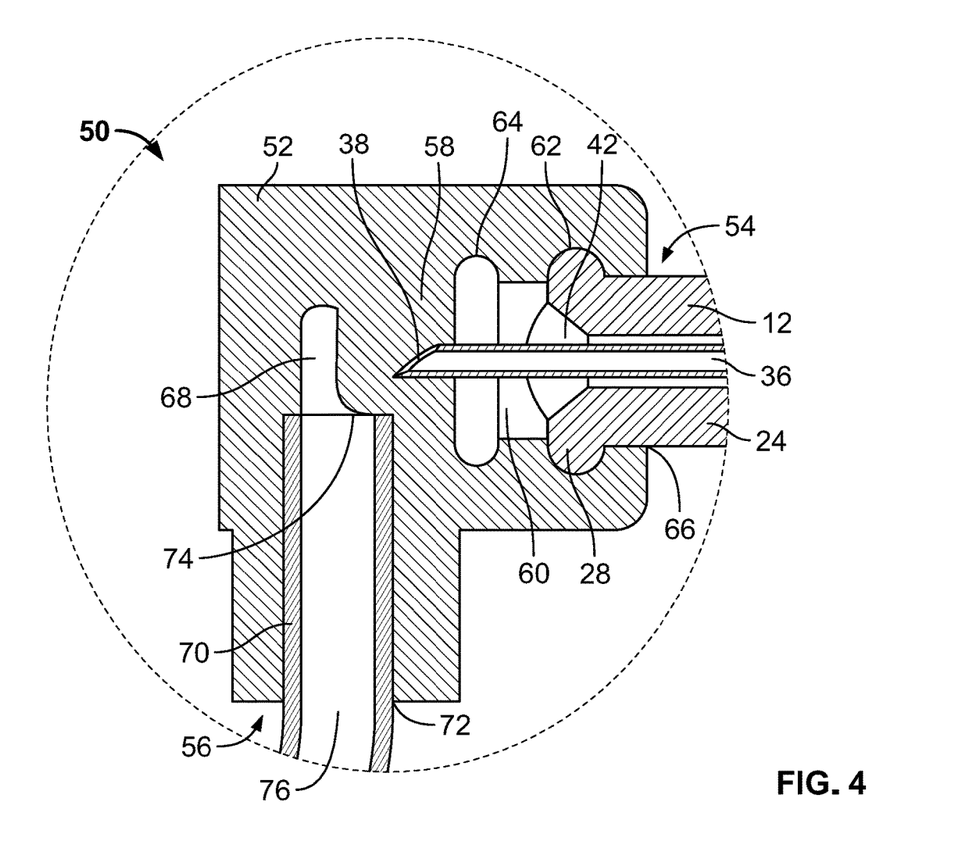
FIG. 4 is a partial view of FIG. 3.

Among particular illustrative proteins are the specific proteins set forth below, including fusions, fragments, analogs, variants or derivatives thereof:

OPGL specific antibodies, peptibodies, and related proteins, and the like (also referred to as RANKL specific antibodies, peptibodies and the like), including fully humanized and human OPGL specific antibodies, particularly fully humanized monoclonal antibodies, including but not limited to the antibodies described in PCT Publication No. WO 03/002713, which is incorporated herein in its entirety as to OPGL specific antibodies and antibody related proteins, particularly those having the sequences set forth therein, particularly, but not limited to, those denoted therein: 9H7; 18B2; 2D8; 2E11; 16E1; and 22B3, including the OPGL specific antibodies having either the light chain of SEQ ID NO:2 as set forth therein in FIG. 2 and/or the heavy chain of SEQ ID NO:4, as set forth therein in FIG. 4, each of which is individually and specifically incorporated by reference herein in its entirety fully as disclosed in the foregoing publication;

Myostatin binding proteins, peptibodies, and related proteins, and the like, including myostatin specific peptibodies, particularly those described in U.S. Publication No. 2004/0181033 and PCT Publication No. WO 2004/058988, which are incorporated by reference herein in their entirety particularly in parts pertinent to myostatin specific peptibodies, including but not limited to peptibodies of the mTN8-19 family, including those of SEQ ID NOS:305-351, including TN8-19-1 through TN8-19-40, TN8-19 con1 and TN8-19 con2; peptibodies of the mL2 family of SEQ ID NOS:357-383; the mL15 family of SEQ ID NOS:384-409; the mL17 family of SEQ ID NOS: 410-438; the mL20 family of SEQ ID NOS: 439-446; the mL21 family of SEQ ID NOS:447-452; the mL24 family of SEQ ID NOS:453-454; and those of SEQ ID NOS:615-631, each of which is individually and specifically incorporated by reference herein in their entirety fully as disclosed in the foregoing publication;

IL-4 receptor specific antibodies, peptibodies, and related proteins, and the like, particularly those that inhibit activities mediated by binding of IL-4 and/or IL-13 to the receptor, including those described in PCT Publication No. WO 2005/047331 or PCT Application No. PCT/US2004/37242 and in U.S. Publication No. 2005/112694, which are incorporated herein by reference in their entirety particularly in parts pertinent to IL-4 receptor specific antibodies, particularly such antibodies as are described therein, particularly, and without limitation, those designated therein: L1H1; L1H2; L1H3; L1H4; L1H5; L1H6; L1H7; L1H8; L1H9; L1H10; L1H11; L2H1; L2H2; L2H3; L2H4; L2H5; L2H6; L2H7; L2H8; L2H9; L2H10; L2H11; L2H12; L2H13; L2H14; L3H1; L4H1; L5H1; L6H1, each of which is individually and specifically incorporated by reference herein in its entirety fully as disclosed in the foregoing publication;

Interleukin 1-receptor 1 ("IL1-R1") specific antibodies, peptibodies, and related proteins, and the like, including but not limited to those described in U.S. Publication No. 2004/097712, which is incorporated herein by reference in its entirety in parts pertinent to IL1-R1 specific binding proteins, monoclonal antibodies in particular, especially, without limitation, those designated therein: 15CA, 26F5, 27F2, 24E12, and 10H7, each of which is individually and specifically incorporated by reference herein in its entirety fully as disclosed in the aforementioned publication;

Ang2 specific antibodies, peptibodies, and related proteins, and the like, including but not limited to those described in PCT Publication No. WO 03/057134 and U.S. Publication No. 2003/0229023, each of which is incorporated herein by reference in its entirety particularly in parts pertinent to Ang2 specific antibodies and peptibodies and the like, especially those of sequences described therein and including but not limited to: L1(N); L1(N) WT; L1(N) 1K WT; 2xL1(N); 2xL1(N) WT; Con4 (N), Con4 (N) 1K WT, 2xCon4 (N) 1K; L1C; L1C 1K; 2xL1C; Con4C; Con4C 1K; 2xCon4C 1K; Con4-L1 (N); Con4-L1C; TN-12-9 (N); C17 (N); TN8-8(N); TN8-14 (N); Con 1 (N), also including anti-Ang 2 antibodies and formulations such as those described in PCT Publication No. WO 2003/030833 which is incorporated herein by reference in its entirety as to the same, particularly Ab526; Ab528; Ab531; Ab533; Ab535; Ab536; Ab537; Ab540; Ab543; Ab544; Ab545; Ab546; A551; Ab553; Ab555; Ab558; Ab559; Ab565; AbF1AbFD; AbFE; AbFJ; AbFK; AbG1D4; AbGC1E8; AbH1C12; AblA1; AblF; AblK, AblP; and AblP, in their various permutations as described therein, each of which is individually and specifically incorporated by reference herein in its entirety fully as disclosed in the foregoing publication;

NGF specific antibodies, peptibodies, and related proteins, and the like including, in particular, but not limited to those described in U.S. Publication No. 2005/0074821 and U.S. Pat. No. 6,919,426, which are incorporated herein by reference in their entirety particularly as to NGF-specific antibodies and related proteins in this regard, including in particular, but not limited to, the NGF-specific antibodies therein designated 4D4, 4G6, 6H9, 7H2, 14D10 and 14D11, each of which is individually and specifically incorporated by reference herein in its entirety fully as disclosed in the foregoing publication;

CD22 specific antibodies, peptibodies, and related proteins, and the like, such as those described in U.S. Pat. No. 5,789,554, which is incorporated herein by reference in its entirety as to CD22 specific antibodies and related proteins, particularly human CD22 specific antibodies, such as but not limited to humanized and fully human antibodies, including but not limited to humanized and fully human monoclonal antibodies, particularly including but not limited to human CD22 specific IgG antibodies, such as, for instance, a dimer of a human-mouse monoclonal hLL2 gamma-chain disulfide linked to a human-mouse monoclonal hLL2 kappa-chain, including, but limited to, for example, the human CD22 specific fully humanized antibody in Epratuzumab, CAS registry number 501423-23-0;

IGF-1 receptor specific antibodies, peptibodies, and related proteins, and the like, such as those described in PCT Publication No. WO 06/069202, which is incorporated herein by reference in its entirety as to IGF-1 receptor specific antibodies and related proteins, including but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, L52H52, and IGF-1R-binding fragments and derivatives thereof, each of which is individually and specifically incorporated by reference herein in its entirety fully as disclosed in the foregoing publication;

Also among non-limiting examples of anti-IGF-1R antibodies for use in the methods and compositions of the present invention are each and all of those described in:

U.S. Publication No. 2006/0040358 (published Feb. 23, 2006), 2005/0008642 (published Jan. 13, 2005), 2004/0228859 (published Nov. 18, 2004), including but not limited to, for instance, antibody 1A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein;

PCT Publication No. WO 06/138729 (published Dec. 28, 2006) and WO 05/016970 (published Feb. 24, 2005), and Lu et al. (2004), J. Biol. Chem. 279:2856-2865, including but not limited to antibodies 2F8, A12, and IMC-A12 as described therein;

PCT Publication No. WO 07/012614 (published Feb. 1, 2007), WO 07/000328 (published Jan. 4, 2007), WO 06/013472 (published Feb. 9, 2006), WO 05/058967 (published Jun. 30, 2005), and WO 03/059951 (published Jul. 24, 2003);

U.S. Publication No. 2005/0084906 (published Apr. 21, 2005), including but not limited to antibody 7C10, chimaeric antibody C7C10, antibody h7C10, antibody 7H2M, chimaeric antibody *7C10, antibody GM 607, humanized antibody 7C10 version 1, humanized antibody 7C10 version 2, humanized antibody 7C10 version 3, and antibody 7H2HM, as described therein;

U.S. Publication Nos. 2005/0249728 (published Nov. 10, 2005), 2005/0186203 (published Aug. 25, 2005), 2004/0265307 (published Dec. 30, 2004), and 2003/0235582 (published Dec. 25, 2003) and Maloney et al. (2003), Cancer Res. 63:5073-5083, including but not limited to antibody EM164, resurfaced EM164, humanized EM164, huEM164 v1.0, huEM164 v1.1, huEM164 v1.2, and huEM164 v1.3 as described therein;

U.S. Pat. No. 7,037,498 (issued May 2, 2006), U.S. Publication Nos. 2005/0244408 (published Nov. 30, 2005) and 2004/0086503 (published May 6, 2004), and Cohen, et al. (2005), Clinical Cancer Res. 11:2063-2073, e.g., antibody CP-751,871, including but not limited to each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1, 4.9.2, and 4.17.3, as described therein;

U.S. Publication Nos. 2005/0136063 (published Jun. 23, 2005) and 2004/0018191 (published Jan. 29, 2004), including but not limited to antibody 19D12 and an antibody comprising a heavy chain encoded by a polynucleotide in plasmid 15H12/19D12 HCA (y4), deposited at the ATCC under number PTA-5214, and a light chain encoded by a polynucleotide in plasmid 15H12/19D12 LCF (K), deposited at the ATCC under number PTA-5220, as described therein; and U.S. Publication No. 2004/0202655 (published Oct. 14, 2004), including but not limited to antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT-11A5, PINT-11A7, PINT-11A12, PINT-12A1, PINT-12A2, PINT-12A3, PINT-12A4, and PINT-12A5, as described therein; each and all of which are herein incorporated by reference in their entireties, particularly as to the aforementioned antibodies, peptibodies, and related proteins and the like that target IGF-1 receptors;

B-7 related protein 1 specific antibodies, peptibodies, related proteins and the like ("B7RP-1," also is referred to in the literature as B7H2, ICOSL, B7h, and CD275), particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, ICOS, on activated T cells in particular, especially, in all of the foregoing regards, those disclosed in U.S. Publication No. 2008/0166352 and PCT Publication No. WO 07/011941, which are incorporated herein by reference in their entireties as to such antibodies and related proteins, including but not limited to antibodies designated therein as follow: 16H (having light chain variable and heavy chain variable sequences SEQ ID NO:1 and SEQ ID NO:7 respectively therein); 5D (having light chain variable and heavy chain variable sequences SEQ ID NO:2 and SEQ ID NO:9 respectively therein); 2H (having light chain variable and heavy chain variable sequences SEQ ID NO:3 and SEQ ID NO: 10 respectively therein); 43H (having light chain variable and heavy chain variable sequences SEQ ID NO:6 and SEQ ID NO:14 respectively therein); 41H (having light chain variable and heavy chain variable sequences SEQ ID NO:5 and SEQ ID NO:13 respectively therein); and 15H (having light chain variable and heavy chain variable sequences SEQ ID NO:4 and SEQ ID NO:12 respectively therein), each of which is individually and specifically incorporated by reference herein in its entirety fully as disclosed in the foregoing publication;

IL-15 specific antibodies, peptibodies, and related proteins, and the like, such as, in particular, humanized monoclonal antibodies, particularly antibodies such as those disclosed in U.S. Publication Nos. 2003/0138421; 2003/023586; and 2004/0071702; and U.S. Pat. No. 7,153,507, each of which is incorporated herein by reference in its entirety as to IL-15 specific antibodies and related proteins, including peptibodies, including particularly, for instance, but not limited to, HuMax IL-15 antibodies and related proteins, such as, for instance, 146B7;

IFN gamma specific antibodies, peptibodies, and related proteins and the like, especially human IFN gamma specific antibodies, particularly fully human anti-IFN gamma antibodies, such as, for instance, those described in U.S. Publication No. 2005/0004353, which is incorporated herein by reference in its entirety as to IFN gamma specific antibodies, particularly, for example, the antibodies therein designated 1118; 1118*; 1119; 1121; and 1121*. The entire sequences of the heavy and light chains of each of these antibodies, as well as the sequences of their heavy and light chain variable regions and complementarity determining regions, are each individually and specifically incorporated by reference herein in its entirety fully as disclosed in the foregoing publication and in Thakur et al. (1999), Mol. Immunol. 36:1107-1115. In addition, description of the properties of these antibodies provided in the foregoing publication is also incorporated by reference herein in its entirety. Specific antibodies include those having the heavy chain of SEQ ID NO: 17 and the light chain of SEQ ID NO: 18; those having the heavy chain variable region of SEQ ID NO:6 and the light chain variable region of SEQ ID NO:8; those having the heavy chain of SEQ ID NO: 19 and the light chain of SEQ ID NO:20; those having the heavy chain variable region of SEQ ID NO: 10 and the light chain variable region of SEQ ID NO: 12; those having the heavy chain of SEQ ID NO:32 and the light chain of SEQ ID NO:20; those having the heavy chain variable region of SEQ ID NO:30 and the light chain variable region of SEQ ID NO: 12; those having the heavy chain sequence of SEQ ID NO:21 and the light chain sequence of SEQ ID NO:22; those having the heavy chain variable region of SEQ ID NO: 14 and the light chain variable region of SEQ ID NO: 16; those having the heavy chain of SEQ ID NO:21 and the light chain of SEQ ID NO:33; and those having the heavy chain variable region of SEQ ID NO: 14 and the light chain variable region of SEQ ID NO:31, as disclosed in the foregoing publication. A specific antibody contemplated is antibody 1119 as disclosed in the foregoing U.S. publication and having a complete heavy chain of SEQ ID NO: 17 as disclosed therein and having a complete light chain of SEQ ID NO: 18 as disclosed therein;

TALL-1 specific antibodies, peptibodies, and the related proteins, and the like, and other TALL specific binding proteins, such as those described in U.S. Publication Nos. 2003/0195156 and 2006/0135431, each of which is incorporated herein by reference in its entirety as to TALL-1 binding proteins, particularly the molecules of Tables 4 and 5B, each of which is individually and specifically incorporated by reference herein in its entirety fully as disclosed in the foregoing publications;

Parathyroid hormone ("PTH") specific antibodies, peptibodies, and related proteins, and the like, such as those described in U.S. Pat. No. 6,756,480, which is incorporated herein by reference in its entirety, particularly in parts pertinent to proteins that bind PTH;

Thrombopoietin receptor ("TPO-R") specific antibodies, peptibodies, and related proteins, and the like, such as those described in U.S. Pat. No. 6,835,809, which is herein incorporated by reference in its entirety, particularly in parts pertinent to proteins that bind TPO-R;

Hepatocyte growth factor ("HGF") specific antibodies, peptibodies, and related proteins, and the like, including those that target the HGF/SF:cMet axis (HGF/SF:c-Met), such as the fully human monoclonal antibodies that neutralize hepatocyte growth factor/scatter (HGF/SF) described in U.S. Publication No. 2005/0118643 and PCT Publication No. WO 2005/017107, huL2G7 described in U.S. Pat. No. 7,220,410 and OA-5d5 described in U.S. Pat. Nos. 5,686,292 and 6,468,529 and in PCT Publication No. WO 96/38557, each of which is incorporated herein by reference in its entirety, particularly in parts pertinent to proteins that bind HGF;

TRAIL-R2 specific antibodies, peptibodies, related proteins and the like, such as those described in U.S. Pat. No. 7,521,048, which is herein incorporated by reference in its entirety, particularly in parts pertinent to proteins that bind TRAIL-R2;

Activin A specific antibodies, peptibodies, related proteins, and the like, including but not limited to those described in U.S. Publication No. 2009/0234106, which is herein incorporated by reference in its entirety, particularly in parts pertinent to proteins that bind Activin A;

TGF-beta specific antibodies, peptibodies, related proteins, and the like, including but not limited to those described in U.S. Pat. No. 6,803,453 and U.S. Publication No. 2007/0110747, each of which is herein incorporated by reference in its entirety, particularly in parts pertinent to proteins that bind TGF-beta;

Amyloid-beta protein specific antibodies, peptibodies, related proteins, and the like, including but not limited to those described in PCT Publication No. WO 2006/081171, which is herein incorporated by reference in its entirety, particularly in parts pertinent to proteins that bind amyloid-beta proteins. One antibody contemplated is an antibody having a heavy chain variable region comprising SEQ ID NO:8 and a light chain variable region having SEQ ID NO:6 as disclosed in the foregoing publication;

c-Kit specific antibodies, peptibodies, related proteins, and the like, including but not limited to those described in U.S. Publication No. 2007/0253951, which is incorporated herein by reference in its entirety, particularly in parts pertinent to proteins that bind c-Kit and/or other stem cell factor receptors;

OX40L specific antibodies, peptibodies, related proteins, and the like, including but not limited to those described in U.S. Publication No. 2006/0002929, which is herein incorporated by reference in its entirety, particularly in parts pertinent to proteins that bind OX40L and/or other ligands of the OX40 receptor; and Other exemplary proteins, including Activase® (alteplase, tPA); Aranesp® (darbepoetin alfa); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4ß7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-C5 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Neulasta® (pegylated filgrastim, pegylated G-CSF, pegylated hu-Met-G-CSF); Neupogen® (filgrastim, G-CSF, hu-MetG-CSF); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/IIIa receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL15 antibody, see U.S. Pat. No. 7,153,507); Tysabri® (natalizumab, anti-α4integrin mAb); Valortim® (MDX-1303, anti-*B. anthracis* protective antigen mAb); ABthrax™; Vectibix® (panitumumab); Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Rα mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-531 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); anti-LLY antibody; BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFß mAb (GC-1008); anti-TRAIL Receptor-2 human mAb (HGS-ETR2); anti-TWEAK mAb; anti-VEGFR/FIt-1 mAb; anti-ZP3 mAb (HuMax-ZP3); NVS Antibody #1; and NVS Antibody #2.

Also included can be a sclerostin antibody, such as but not limited to romosozumab, blosozumab, or BPS 804 (Novartis). Further included can be therapeutics such as rilotumumab, bixalomer, trebananib, ganitumab, conatumumab, motesanib diphosphate, brodalumab, vidupiprant, panitumumab, denosumab, NPLATE, PROLIA, VECTIBIX or XGEVA.

Additionally, included in the device can be a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab), as well as molecules, variants, analogs or derivatives thereof as disclosed in the following patents or patent applications, each of which is herein incorporated by reference in its entirety for all purposes: U.S. Pat. No. 8,030,547, U.S. Publication No. 2013/0064825, WO2008/057457, WO2008/057458, WO2008/057459, WO2008/063382, WO2008/133647, WO2009/100297, WO2009/100318, WO2011/037791, WO2011/053759, WO2011/053783, WO2008/125623, WO2011/072263, WO2009/055783, WO2012/0544438, WO2010/029513, WO2011/111007, WO2010/077854, WO2012/088313, WO2012/101251, WO2012/101252, WO2012/101253, WO2012/109530, and WO2001/031007.

Also included can be talimogene laherparepvec or another oncolytic HSV for the treatment of melanoma or other cancers. Examples of oncolytic HSV include, but are not limited to talimogene laherparepvec (U.S. Pat. Nos. 7,223,593 and 7,537,924); OncoVEXGALV/CD (U.S. Pat. No. 7,981,669); OrienX010 (Lei et al. (2013), World J. Gastroenterol., 19:5138-5143); G207, 1716; NV1020; NV12023; NV1034 and NV1042 (Vargehes et al. (2002), Cancer Gene Ther., 9(12):967-978).

Also included are TIMPs. TIMPs are endogenous tissue inhibitors of metalloproteinases (TIMPs) and are important in many natural processes. TIMP-3 is expressed by various cells or and is present in the extracellular matrix; it inhibits all the major cartilage-degrading metalloproteases, and may play a role in role in many degradative diseases of connective tissue, including rheumatoid arthritis and osteoarthritis, as well as in cancer and cardiovascular conditions. The amino acid sequence of TIMP-3, and the nucleic acid sequence of a DNA that encodes TIMP-3, are disclosed in U.S. Pat. No. 6,562,596, issued May 13, 2003, the disclosure of which is incorporated by reference herein. Description of TIMP mutations can be found in U.S. Publication No. 2014/0274874 and PCT Publication No. WO 2014/152012.

Also included are antagonistic antibodies for human calcitonin gene-related peptide (CGRP) receptor and bispecific antibody molecule that target the CGRP receptor and other headache targets. Further information concerning these molecules can be found in PCT Application No. WO 2010/075238.

Additionally, bispecific T cell engager (BiTE®) antibodies, e.g. BLINCYTO® (blinatumomab), can be used in the device. Alternatively, included can be an APJ large molecule agonist e.g., apelin or analogues thereof in the device. Information relating to such molecules can be found in PCT Publication No. WO 2014/099984.

In certain embodiments, the medicament comprises a therapeutically effective amount of an anti-thymic stromal lymphopoietin (TSLP) or TSLP receptor antibody. Examples of anti-TSLP antibodies that may be used in such embodiments include, but are not limited to, those described in U.S. Pat. Nos. 7,982,016, and 8,232,372, and U.S. Publication No. 2009/0186022. Examples of anti-TSLP receptor antibodies include, but are not limited to, those described in U.S. Pat. No. 8,101,182. In particularly preferred embodiments, the medicament comprises a therapeutically effective amount of the anti-TSLP antibody designated as A5 within U.S. Pat. No. 7,982,016.

Although the components, assemblies, drug delivery devices, and methods, have been described in terms of exemplary embodiments, they are not limited thereto. The detailed description is to be construed as exemplary only and does not describe every possible embodiment of the invention because describing every possible embodiment would be impractical, if not impossible. Numerous alternative embodiments could be implemented, using either current technology or technology developed after the filing date of this patent that would still fall within the scope of the claims defining the invention. For example, components described herein with reference to certain kinds of drug delivery devices, such as on-body injector drug delivery devices or other kinds of drug delivery devices, can also be utilized in other kinds of drug delivery devices, such as autoinjector drug delivery devices.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

What is claimed is:

1. A fluid path assembly for a drug delivery device, the fluid path assembly comprising:
   a reservoir having a sidewall defining an interior for containing a drug and a neck at a first end;
   a needle fixed within the neck of the reservoir with a first end extending forwardly from the reservoir and a second end fluidly connected to the interior of the reservoir, the needle prevented from moving relative to the neck;
   a needle shield valve member having a body defining an inlet coupled to the reservoir, an outlet, and a barrier extending between the inlet and the outlet to prevent fluid flow through the body, wherein at least one of the reservoir and the needle shield valve member is movable between a first position where the needle is embedded within or spaced from the barrier and a second position where the needle extends through the barrier to establish a fluid path from the interior of the reservoir to the outlet of the body.

2. The fluid path assembly of claim 1, wherein the reservoir is movable between the first position and the second position.

3. The fluid path assembly of claim 1, wherein the needle is embedded within the barrier in the first position.

4. The fluid path assembly of claim 1, wherein the reservoir includes a flange extending outwardly around the first end of the sidewall; and the inlet of the needle shield valve member includes a first internal groove to engage the flange in the first position and a second internal groove to engage the flange in the second position.

5. The fluid path assembly of claim 1, wherein the body of the needle shield valve member has an axis of the outlet disposed at a ninety degree angle or less with respect to an axis of the inlet.

6. The fluid path assembly of claim 1, wherein the body of the needle shield valve member comprises a material permeable by a sterilization gas.

7. The fluid path assembly of claim 1, wherein the first end of the sidewall includes an end wall tapering to the neck; and further comprising a stopper disposed within the interior of the reservoir, the stopper includes a forward surface having a contour complementary to the end wall.

8. The fluid path assembly of claim 1, wherein the body of the needle shield valve member has a single piece construction.

9. The fluid path assembly of claim 1, wherein the outlet of the body includes a reduced width needle reception portion, a conduit reception portion, and a shoulder extending between the conduit reception portion and the needle reception portion.

10. The fluid path assembly of claim 9, further comprising a conduit disposed within the outlet to abut the shoulder.

11. The fluid path assembly of claim 1, further comprising a needle shield cover surrounding at least a portion of the body of the needle shield valve member.

12. The fluid path assembly of claim 11, wherein the needle shield cover includes a body having a length greater than that of the body of the needle shield valve member.

13. The fluid path assembly of claim 1, further comprising a drive mechanism configured to move at least one of the reservoir and the needle shield valve member from the first position to the second position.

14. The fluid path assembly of claim 13 in combination with a drug delivery device, the drug delivery device comprising:
 a housing;
 a needle insertion mechanism; and
 a plunger drive mechanism configured to selectively drive the stopper through the container to thereby force the drug from the reservoir with the reservoir in the second position.

15. A method of establishing a fluid flow path in a drug delivery device including a reservoir having a sidewall defining an interior for containing a drug and a first end, a needle fixed within the first end of the reservoir with a first end extending forwardly from the reservoir and a second end fluidly connected to the interior of the reservoir, and a needle shield valve member having a body defining an inlet coupled to the reservoir, an outlet, and a barrier extending between the inlet and the outlet to prevent fluid flow through the body, wherein the needle is prevented from moving relative to the neck, the method comprising:
 coupling the reservoir to the inlet of the body in a first position so that a tip of the needle is embedded within or spaced from the barrier;
 moving at least one of the reservoir and the needle shield valve member to a second position so that the tip of the needle extends through the barrier to establish a fluid flow path from the interior of the reservoir to the outlet of the body.

16. The method of claim 15, wherein coupling the reservoir to the inlet of the body in the first position comprises embedding the tip of the needle within the barrier.

17. The method of claim 15, wherein the reservoir includes a neck at the first end and a flange extending outwardly around the neck; and the inlet of the needle shield valve member includes first and second internal grooves, and
 wherein coupling the reservoir to the inlet of the body in the first position comprises disposing the flange within the first internal groove; and moving at least one of the reservoir and the needle shield valve member to the second position comprises moving the flange to the second internal groove.

18. The method of claim 15, further comprising sterilizing the reservoir, needle, and needle shield valve member.

19. The method of claim 15, further comprising inserting a conduit into the outlet of the needle shield valve member until the conduit abuts a shoulder extending between a conduit reception portion and a needle reception portion of the outlet.

20. The method of claim 15, further comprising driving a stopper through the reservoir to dispense a drug through the needle and into the outlet of the needle shield valve member, comprising engaging a tapering end wall of the first end of the reservoir with a forward surface of the stopper having a contour complementary to the end wall such that hold up volume of the drug within the reservoir is limited to drug remaining in the needle.

\* \* \* \* \*

UNITED STATES PATENT AND TRADEMARK OFFICE
CERTIFICATE OF CORRECTION

PATENT NO. : 12,109,389 B2
APPLICATION NO. : 17/256240
DATED : October 8, 2024
INVENTOR(S) : Matthew Wayne Janke et al.

Page 1 of 1

It is certified that error appears in the above-identified patent and that said Letters Patent is hereby corrected as shown below:

On the Title Page

At item (72), Lines 8-9, "Robert Allen Dees," should be -- Robert Allen Dees, Deceased, --.

Signed and Sealed this
Eighteenth Day of November, 2025

John A. Squires
*Director of the United States Patent and Trademark Office*